(12) United States Patent
Goren

(10) Patent No.: US 7,586,599 B2
(45) Date of Patent: Sep. 8, 2009

(54) METHOD AND SYSTEM FOR DETECTING DEFECTS

(75) Inventor: Tsvi Goren, Ness-Tziona (IL)

(73) Assignee: Applied Materials, Isreal, Ltd., Rehovot (IL)

( * ) Notice: Subject to any disclaimer, the term of this patent is extended or adjusted under 35 U.S.C. 154(b) by 448 days.

(21) Appl. No.: 11/463,261

(22) Filed: Aug. 8, 2006

(65) Prior Publication Data

US 2007/0070335 A1 Mar. 29, 2007

Related U.S. Application Data

(60) Provisional application No. 60/706,549, filed on Aug. 8, 2005.

(51) Int. Cl.
*G01N 21/00* (2006.01)

(52) U.S. Cl. .................... 356/237.5; 356/237.4

(58) Field of Classification Search ............. None
See application file for complete search history.

(56) References Cited

U.S. PATENT DOCUMENTS

| | | | | |
|---|---|---|---|---|
| 5,712,701 A | * | 1/1998 | Clementi et al. | 356/237.2 |
| 6,118,525 A | * | 9/2000 | Fossey et al. | 356/237.2 |
| 6,246,787 B1 | * | 6/2001 | Hennessey et al. | 356/237.1 |
| 6,263,292 B1 | * | 7/2001 | Fiekowsky | 702/95 |
| 6,870,169 B2 | * | 3/2005 | Obara et al. | 356/237.1 |
| 7,187,436 B2 | * | 3/2007 | Harding et al. | 356/237.2 |
| 7,242,467 B2 | * | 7/2007 | Wienecke | 356/237.5 |

* cited by examiner

*Primary Examiner*—Gregory J Toatley, Jr.
*Assistant Examiner*—Juan D Valentin
(74) *Attorney, Agent, or Firm*—Tarek N. Fahmi

(57) ABSTRACT

A method for defect detection includes: (i) scanning at least one wafer by a monitoring system and providing defect size information for each defect that belongs to a group of defects; (ii) scanning the at least one wafer by a wafer inspection system that includes multiple detectors and providing a set of defect detection signals for each defect of the group, wherein the wafer inspection system is characterized by lower resolution than the monitoring system; (iii) classifying the defects to defect classes; (iv) determining multiple relationships between defect types, defect sizes and sets of detection signals; (v) scanning a second wafer by the wafer inspection tool; and (vi) generating, for multiple defects, second wafer defect size information in response to the determined relationships and in response to multiple sets of detection signals generated during the scanning of the second wafer.

11 Claims, 5 Drawing Sheets

METHOD AND SYSTEM FOR DETECTING DEFECTS

RELATED APPLICATION

This application is a NON-PROVISIONAL of, incorporates by reference herein and claims priority to U.S. Provisional Patent Application 60/706,549, filed 8 Aug. 2005.

FIELD OF THE INVENTION

The present invention relates to wafer inspection systems and to methods for detecting defects, especially dark field inspection methods and systems. The invention is particularly useful for optically scanning patterned semiconductor wafers used in producing integrated-circuit dies or chips, and the invention is therefore described below particularly with respect to this application.

BACKGROUND

Wafer inspection usually includes illuminating a wafer by illumination optics and then collecting and detecting light scattered or reflected from the illuminated wafer. The detection can be performed by one or more sensors to provide one or more detection signals that are then analyzed in order to detect defects.

Wafer inspection methods and systems can differ from each other by their light collection and detection techniques. Bright field inspection systems and methods collect light that is reflected (according to Snell's law) from the illuminated wafer while dark field inspection systems and methods collect light that is scattered from the illuminated wafer. Wafer inspection tools may use imaging or non-imaging detectors. Imaging detectors may include CCD sensors while non-imaging detectors may include PMT detectors.

There is a growing need to increase the throughput of wafer inspection systems, to increase their sensitivity, to enhance type of information that can be generate from a wafer inspection tool, while reducing the cost of these wafer inspection tools or at least reducing the cost of an inspection of a wafer.

Different wafer inspection systems provide different solutions to the above-mentioned contradicting demands. There is a need to provide efficient wafer inspection systems that are capable of providing size information.

SUMMARY OF THE INVENTION

A method for detecting defects includes, in one embodiment, scanning at least one wafer by a monitoring system and providing defect size information for each defect that belongs to a group of defects; scanning the at least one wafer by a wafer inspection system that includes multiple detectors and providing a set of defect detection signals for each defect of the group, wherein the wafer inspection system is characterized by lower resolution than the monitoring system; classifying the defects to defect classes; determining multiple relationships between defect types, defect sizes and sets of detection signals; scanning a second wafer by the wafer inspection tool; and generating, for multiple defects, second wafer defect size information in response to the determined relationships and in response to multiple sets of detection signals generated during the scanning of the second wafer.

In some cases, the method includes determining multiple detector defect size type correlation factors in response to a correlation between defect size, defect type, and at least one detection signal provided by multiple detectors.

In further cases, the stage of generating is responsive to at least one detector defect size type correlation factor.

Also, the stage of providing a set of detection signals may include providing a set of dark field detection signals.

In some embodiments, the stage of determining includes representing the relationships between defect types, defect sizes and sets of detection signals by multiple samples and wherein the providing includes calculating defect size information in response to the samples.

In further embodiments, the stage of scanning the at least one wafer by the monitoring system includes scanning the at least one wafer by a scanning electron microscope.

In still further embodiments, the stage of scanning the at least one wafer by the monitoring system includes scanning the at least one wafer by a high-resolution bright field optical wafer inspection tool.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which.

DETAILED DESCRIPTION OF THE PREFERRED EMBODIMENTS

Reference will now be made in greater detail to exemplary embodiments of the present invention. In the following description made in conjunction with the exemplary embodiments of the present invention, a variety of specific elements are described. The following detailed description is of exemplary embodiments of the invention but the invention is not limited thereto, as modifications and supplemental structures may be added, as would be apparent to those skilled in the art. Also, in the following description of the present invention, a detailed description of known functions and configurations incorporated herein is omitted.

The analysis of detection signals can include defect classification. Various defect classification method and system were developed during the last decade.

Figure 1:
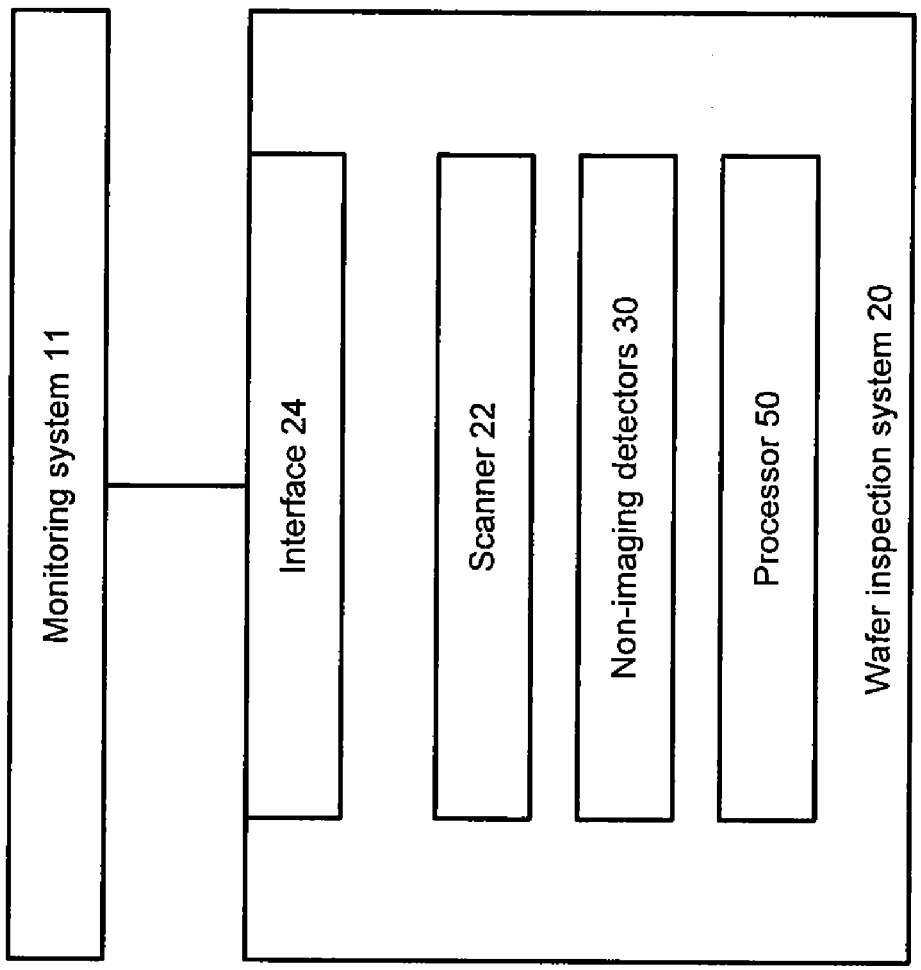
FIG. 1 illustrates a wafer monitoring system, in accordance with an embodiment of the invention.

FIG. 1 illustrates a wafer monitoring system, in accordance with an embodiment of the invention. Wafer monitoring system 10 includes wafer inspection system 20 and monitoring system 11. Monitoring system 11 has a better and even much better resolution than wafer inspection system 20. The monitoring system can be a defect review tool such as a scanning electron microscope (such as but not limited to SEMVision G3 of Applied Materials of Santa Clara, Calif.) and can also be a high resolution optical wafer inspection tool such as but not limited as the UVision of Applied Materials Inc.

Conveniently, monitoring system 11 is adapted to scan at least one wafer and provide defect size information for each defect that belongs to a group of defects. Wafer inspection system 20 includes a scanner 22, adapted to scan the at least one wafer and scan a second wafer; multiple detectors collectively denoted 30 adapted to generates a set of defect detection signals for each defect of the group, and a processor 50 adapted to classify the defects to defect classes, determine multiple relationships between defect types, defect sizes and sets of detection signals. Wafer inspection system 20 is also adapted to generate, for multiple defects, second wafer defect size information in response to the determined relationships and in response to multiple sets of detection signals generated during the scanning of the second wafer. Wafer inspection system 20 is characterized by lower resolution than monitoring system 11.

Wafer inspection system 20 further includes interface 24 for receiving defect size information for each defect that belongs to a wafer pot of the at least one wafer. The defect size information is generated by wafer monitoring system 11.

Figure 2:
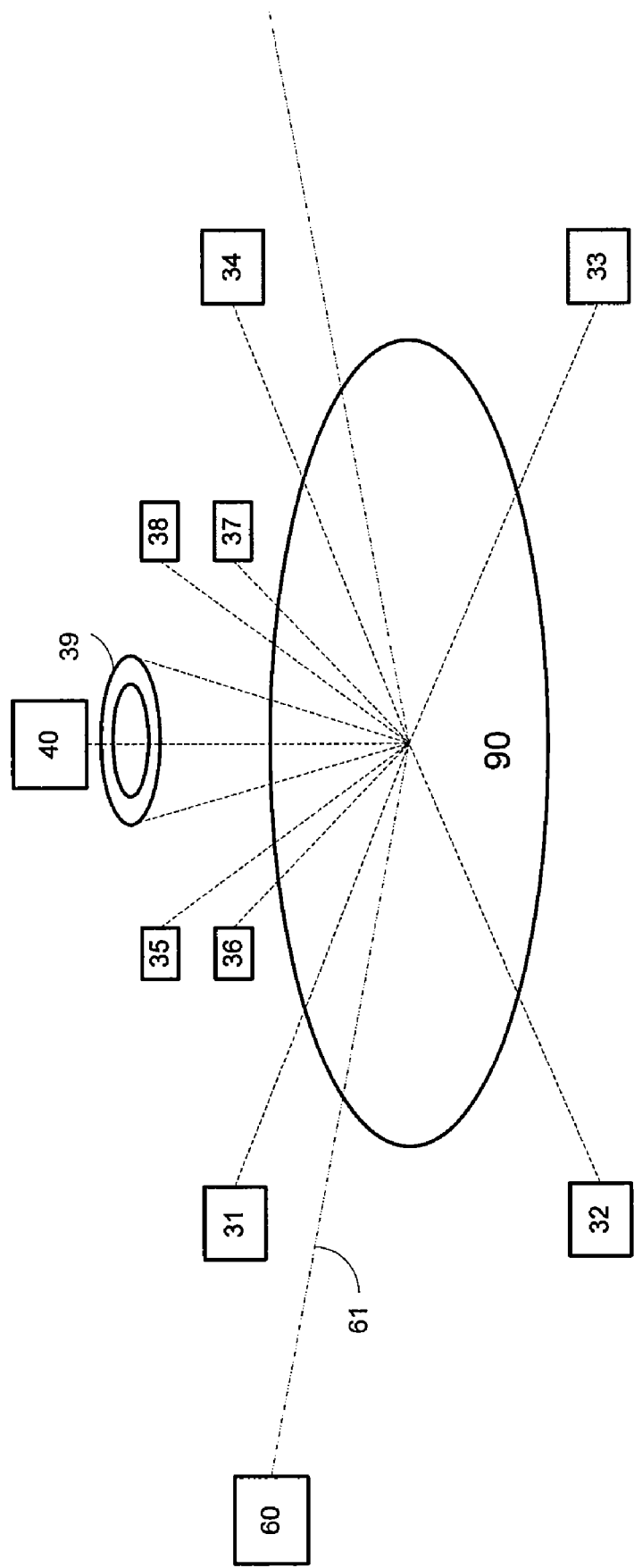
FIG. 2 illustrates an exemplary arrangement of multiple detectors, a wafer and a light source, according to an embodiment of the invention.

FIG. 2 illustrates an exemplary arrangement of multiple detectors 31-40, a wafer 90 and a light source 60, according to an embodiment of the invention.

Light source 60 is provided at a grazing angle to wafer 90. It is noted that light source 60 can also be provided at ninety degrees to wafer 90.

Four detectors 31-34 form a first group of detectors and are provided at a grazing angle, but are arranged spatially away from the normal reflection direction (i.e., Snell's Law reflection) of light beam 61 provided from light source 60.

Four other detectors 35-38 form a second group of detectors and are provided at an intermediate angle (between grazing angle range and between ninety degrees), spatially away from the normal reflection direction of light beam 61. A ring shaped detector 39 is positioned above the second group of detectors but is also spatially away from the normal reflection direction of light beam 61. Another detector is positioned at about ninety degrees to wafer 90.

Detectors 31-40 provide a set of detection signals substantially simultaneously. Thus, once a defect is illuminated a set of detection signals representative of that defect is generated. If the defect spans along multiple pixels than the set of detection signals can include multiple detection signals per detector.

Different detectors can be characterized by different defect size sensitivity. The relationship between an intensity of a detection signal of a detector (or a combination of detection signals of multiple detectors) and the size of the defect is determined during a calibration stage.

It is noted that the response of the detectors may also depend upon the surrounding of the defects and especially the material from which an inspected wafer layer is made of. The inventors found that the relationship between defect size and the intensity of detection signals generated by the detectors differs from metal layers to polysilicon layers, from three-dimensional defects (such as particles that are higher that the surface of the wafer) and from two-dimensional defects (such as very flat residues).

The inventor found that different functions can describe the relationship between defect size and other parameters such as defect type, surroundings (which layer) and the like.

Figure 3:
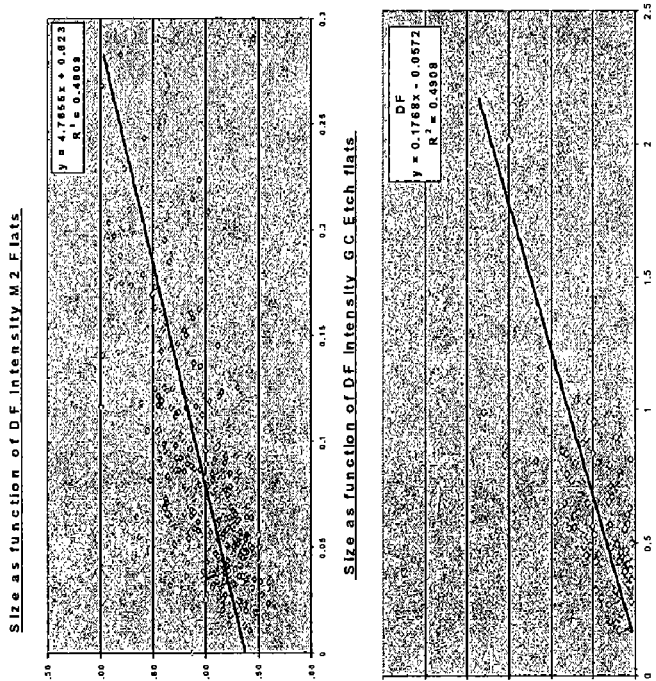
FIG. 3 illustrates various relationships between defect size and detection signals, according to an embodiment of the invention.
Figure 3:
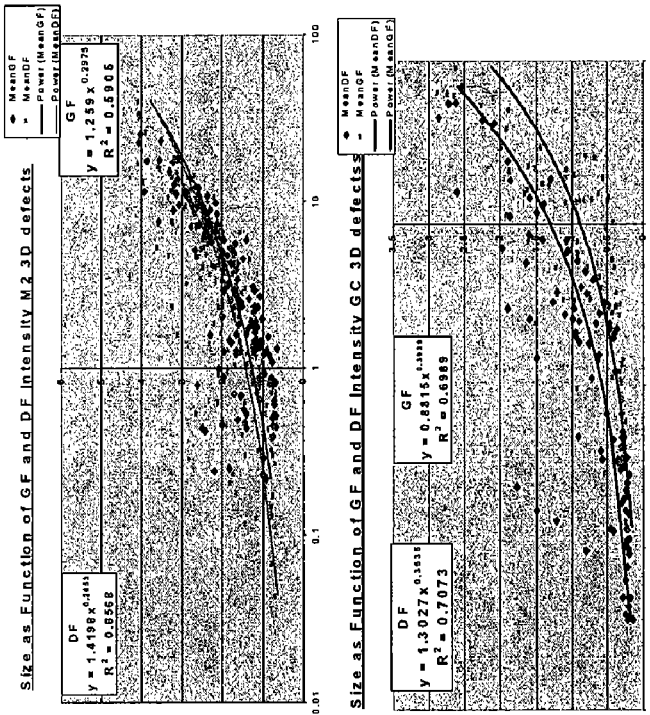

FIG. 3 illustrates various relationships between defect size and detection signals, according to an embodiment of the invention.

The vertical axis (Y axis) of each graph illustrates an intensity level of a detection signal while the horizontal axis (X axis) illustrates the size of defect of a certain type at a certain layer. DF illustrates a combination of detection signals of detectors 31-34 while GF illustrates a combination of detection signals of detectors 35-38.

Each graph includes a curve that approximates the relationship between detection signal intensity and defect size.

Figure 4:
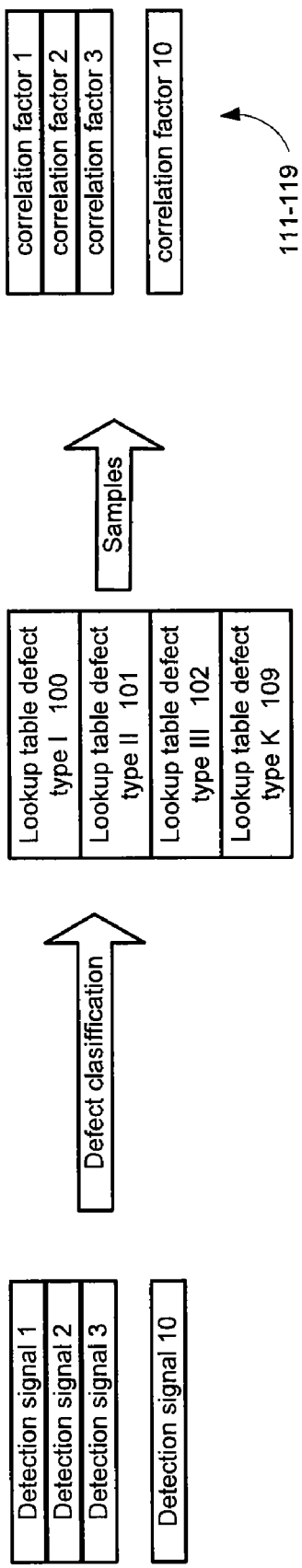
FIG. 4 illustrates multiple data structures, according to an embodiment of the invention.

FIG. 4 illustrates multiple data structures, according to an embodiment of the invention.

Conveniently, the different data structures include lookup tables 100-109 and detector defect size type correlation factor tables 111-119.

Detector defect size type correlation factor tables 110-119 store information that indicate a correlation between an intensity of a detect signal provided by a certain detector and between the size of a certain defect of a certain type. It is noted that such a table can also exist per layer.

Each lookup table out of tables 100-109 (denoted "lookup table defect type I—lookup defect type K") includes multiple samples that represent the relationship between defect type and detection signal intensity (they can represent, for example, the curves illustrated in FIG. 4). Each table includes multiple samples that represent a relationship between defect types, defect sizes and sets of detection signals by multiple samples and wherein the providing comprises calculating defect size information in response to the samples.

Figure 5:
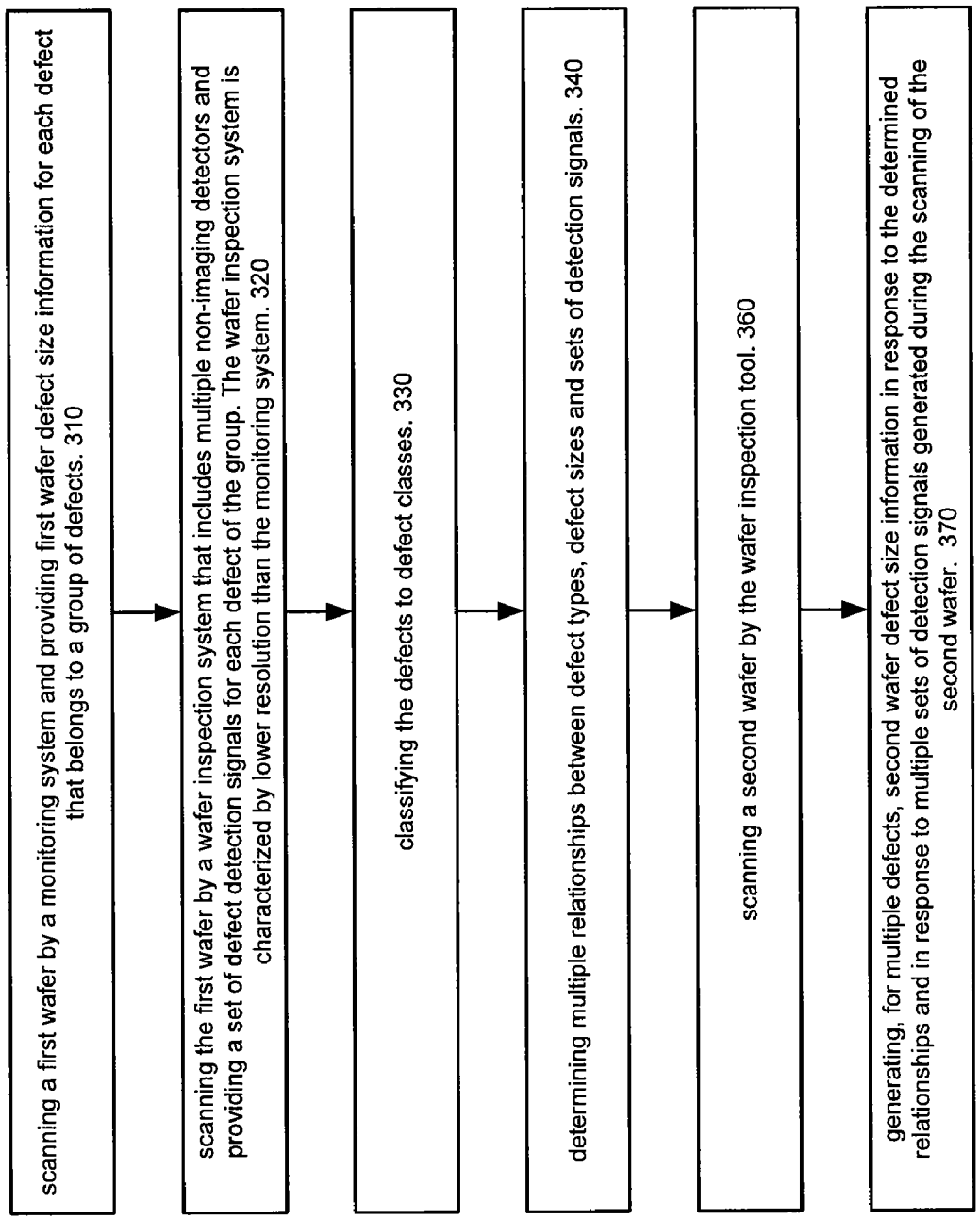
FIG. 5 is a flow chart of a method according to an embodiment of the invention.

FIG. 5 is a flow chart of method 300 according to an embodiment of the invention.

Method 300 starts by stage 310 of scanning at least one wafer (that can form a first set of wafers) and providing defect size information for each defect that belongs to a group of defects. The monitoring system can be a scanning electron microscope, a high resolution optical inspection tool, a high resolution bright field inspection tool that can operate at the deep ultra violet region, and the like. It is noted that the first set of wafers can include one or more wafers. Usually, once enough size information is gathered stage 310 ends. It is noted that statistically, a larger set of wafers can provide more information.

Stage 310 is followed by stage 320 of scanning the at least one wafer by a wafer inspection system that includes multiple detectors and providing a set of defect detection signals for each defect of the group. The wafer inspection system is characterized by lower resolution than the monitoring system. It is noted that the size information gained by the appliance of method 300 can be more accurate than the resolution of the wafer inspection system.

Stage 320 is followed by stage 330 of classifying the defects to defect classes.

Stage 330 is followed by stage 340 of determining multiple relationships between defect types, defect sizes and sets of detection signals. Stage 340 can include determining mathematical functions that can describe the relationship. Various prior art approximation methods can be used. On method include providing a mathematical function, analyzing the distance between detection signals and the mathematical function and determining if the suggested mathematical function provides a sufficient approximation. If the answer is negative approximation process can suggest another mathematical function, can ignore some detection signals (especially those who are relatively remote from the mathematical function) and continue until finding an approximating mathematical function.

Stages 310-340 form a calibration process. Once this process is completed an inspection stage of other wafers can start. Many wafers can then be inspected during the inspection stage, based upon the results of the calibration process.

Stage 340 is followed by stage 360 of scanning a second wafer by the wafer inspection tool.

Stage 360 is followed by stage 370 of generating, for multiple defects, second wafer defect size information in response to the determined relationships and in response to multiple sets of detection signals generated during the scanning of the second wafer.

It is noted that multiple wafers (that differ from second wafer) can be scanned in order to detect defects and to provide defect size information, based upon the results of the calibration process.

Conveniently, stage 340 of determining includes determining multiple detector defect size type correlation factors in response to a correlation between defect size, defect type, and at least one detection signal provided by multiple detectors. For example, if the detection signals of a certain detector are very responsive to the size of a defect of a certain type than if such a defect is detected the size of the defect will be responsive to a detection signal from that detector. Accordingly, stage 370 of generating is responsive to at least one detector defect size type correlation factor.

Conveniently, stage 340 of determining includes representing the relationships between defect types, defect sizes and sets of detection signals by multiple samples and wherein the providing comprises calculating defect size information in response to the samples. It is noted that multiple samples can be stored in data structures such as look up tables.

While this invention has been described in connection with what is presently considered to be the most practical and preferred embodiment, it is to be understood that the invention is not limited to the disclosed embodiment. Rather, it is intended to cover various modifications within the spirit and scope of the appended claims.

What is claimed is:

1. A method for defect detection, the method comprising:
   scanning at least one wafer by a monitoring system and providing defect size information for each defect that belongs to a group of defects;
   scanning the at least one wafer by a wafer inspection system that comprises multiple detectors and providing a set of defect detection signals for each defect of the group, wherein the wafer inspection system is characterized by lower resolution than the monitoring system, classifying the defects to defect classes;
   determining multiple relationships between defect types, defect sizes and sets of detection signals;
   scanning a second wafer by the wafer inspection tool; and
   generating, for multiple defects, second wafer defect size information in response to the determined relationships and in response to multiple sets of detection signals generated during the scanning of the second wafer.

2. The method according to claim 1 wherein the determining also comprises determining multiple detector defect size type correlation factors in response to a correlation between defect size, defect type, and at least one detection signal provided by multiple detectors.

3. The method according to claim 2 wherein the generating is responsive to at least one detector defect size type correlation factor.

4. The method according to claim 1 wherein the providing a set of detection signals comprises providing a set of dark field detection signals.

5. The method according to claim 1 wherein the determining comprises representing the relationships between defect types, defect sizes and sets of detection signals by multiple samples and wherein defect size information is calculated in response to the multiple samples.

6. The method according to claim 1 wherein the stage of scanning the at least one wafer by the monitoring system comprises scanning the at least one wafer by a scanning electron microscope.

7. The method according to claim 1 wherein the stage of scanning the at least one wafer by the monitoring system comprises scanning the at least one wafer by a high-resolution bright field optical wafer inspection tool.

8. A computer program product comprising a computer usable medium comprising a computer readable program wherein the computer readable program when executed on a computer causes the computer to: receive defect size information, generated by a monitoring system for each defect that belongs to a group of defects of at least one wafer; scan the at least one wafer by a wafer inspection system that comprises multiple detectors and provide a set of defect detection signals for each defect of the group, wherein the wafer inspection system is characterized by lower resolution than the monitoring system classify the defects to defect classes; determine multiple relationships between defect types, defect sizes and sets of detection signals; scan a second wafer by the wafer inspection system tool; and generate, for multiple defects, second wafer defect size information in response to the determined relationships and in response to multiple sets of detection signals generated during the scanning of the second wafer; wherein monitoring to classify the defects is performed before scanning the at least one wafer.

9. The computer program product according to claim 8, wherein the computer readable program when executed on a computer causes the computer to determine multiple detector defect size type correlation factors in response to a correlation between defect size, defect type, and at least one detection signal provided by multiple detectors.

10. The computer program product according to claim 8, wherein the computer readable program when executed on a computer causes the computer to generate defect size information in response to at least one detector defect size type correlation factor.

11. The computer program product according to claim 8, wherein the computer readable program when executed on a computer causes the computer to represent the relationships between defect types, defect sizes and sets of detection signals by multiple samples and to calculate defect size information in response to the samples.

* * * * *